United States Patent [19]

Smith

[11] Patent Number: 4,590,376
[45] Date of Patent: May 20, 1986

[54] APPARATUS AND TECHNIQUE FOR MONITORING PHOTOELECTRON EMISSION FROM SURFACES

[75] Inventor: Tennyson Smith, Thousand Oaks, Calif.

[73] Assignee: Photo Acoustic Technology, Inc., Newbury Park, Calif.

[21] Appl. No.: 577,271

[22] Filed: May 30, 1984

[51] Int. Cl.$^4$ ............................................. G01F 23/00
[52] U.S. Cl. .................................... 250/358.1; 250/372
[58] Field of Search ................. 250/336.1, 358.1, 372, 250/492.1, 310; 156/378; 324/158 R, 158 D

[56] References Cited

U.S. PATENT DOCUMENTS

| | | | |
|---|---|---|---|
| 3,549,999 | 12/1970 | Norton | 324/158 D |
| 4,278,508 | 7/1981 | White et al. | 250/372 |
| 4,352,017 | 9/1982 | Duffy et al. | 250/372 |
| 4,393,348 | 7/1983 | Goldstein et al. | 324/158 R |
| 4,447,151 | 5/1984 | McLellan et al. | 356/218 |
| 4,464,627 | 8/1984 | Munakata et al. | 324/158 D |

OTHER PUBLICATIONS

Surface Quality Unit for Inspection by Nondestructive Testing (SQUINT), by Tennyson Smith—published in the National SAMPE Technical Conference, Cincinnati, Fall 1983.
Detecting Contamination with Photoelectron Emission—(Marshall Space Flight Center, Alabama) NASA Tech Briefs, Fall/Winter 1981.
Photoelectron Emission from Aluminum and Nickel Measured in Air Tennyson Smith—Journal of Applied Physics, vol. 46, No. 4, Apr. 1975.
Residual Silicone Detection—Final Report Draft for the Period Nov. 13, 1979–Jul. 12, 1979—Contract No. NAS8-33694 Tennyson Smith–Principal Investigator/-Rockwell International Science Center.

*Primary Examiner*—Janice A. Howell

[57] ABSTRACT

An instrument for monitoring the surface characteristics of materials, whereby the surface is characterized by measurement of a current of photo-emitted electrons flowing from the surface to a collector on the instrument. The instrument directs ultra violet light against the surface being measured, and the photoelectrons emitted are characteristic of surface features such as oxide thickness, contamination, or fatigue. The current of electrons emitted from the surface is compared with previously established limits for surface quality to provide an acceptability test of the surface. The instrument is portable and does not require the use of a vacuum chamber.

13 Claims, 13 Drawing Figures

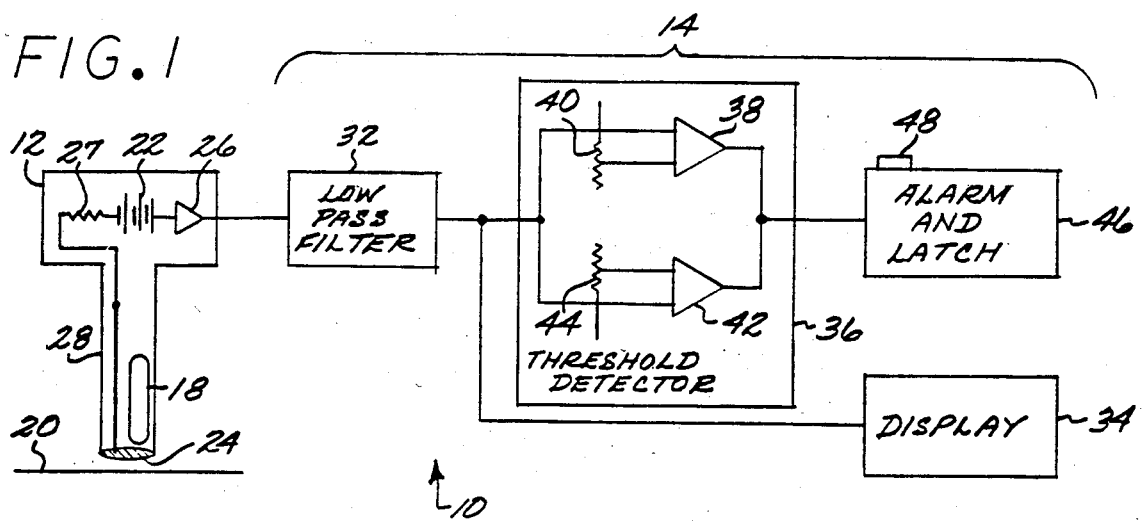
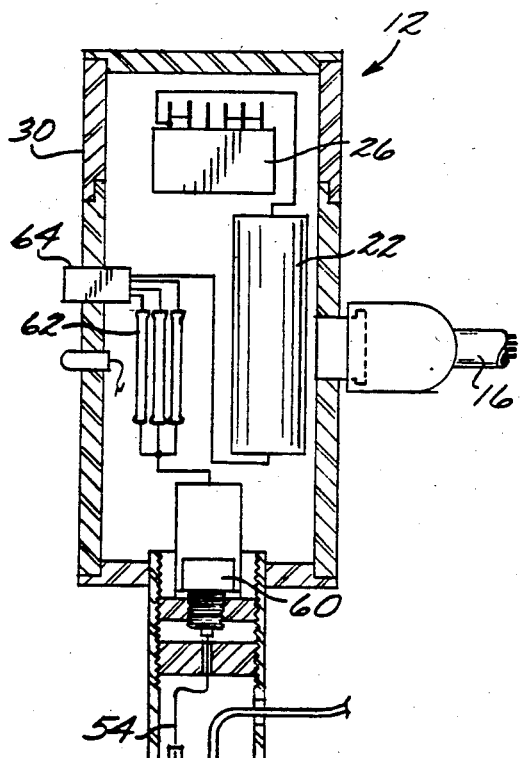
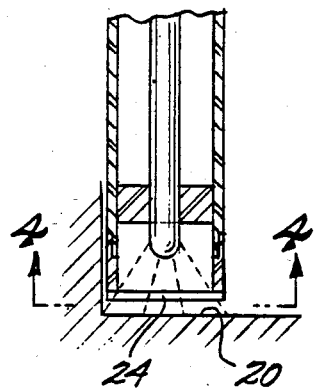
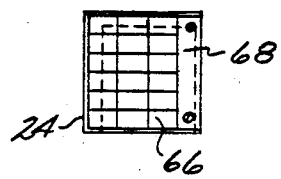
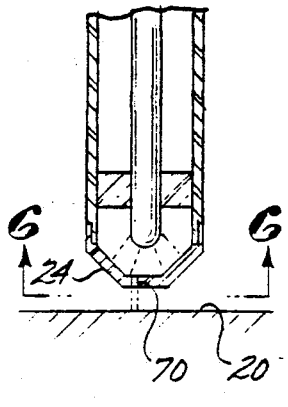
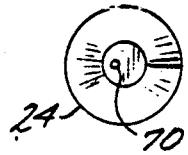

APPARATUS AND TECHNIQUE FOR MONITORING PHOTOELECTRON EMISSION FROM SURFACES

BACKGROUND OF THE INVENTION

This invention relates to measurements of material properties, and, more particularly, to an instrument for use in determining surface characteristics of materials by measuring a current of photoelectronics emitted from a surface.

The quality and condition of its surfaces often determine the suitability of a material for use in an industrial process. To cite some examples, if a material is to be painted or bonded to another material, the presence, type, and amount of contaminants such as grease or dirt often determine the success of the subsequent operation. Coatings or oxides are placed onto the surfaces of semiconductor wafers during the fabrication of microelectronic components, and the thickness of the coating or oxide must be established within critical limits for the success of subsequent operations. The cleanliness of memory disk drive heads must be checked periodically to be certain that contamination does not interfere with read/write functions.

In another setting, the condition of a surface may be a measure of the previous use of the material, and may provide an indicator of its potential for further use. Scratches and abrasion marks on a surface used in bearings and fatigue striations on the surface of a part subjected to cyclical loadings are examples.

In recognition of the critical importance of surfaces, a number of techniques have been developed to observe and measure surface characteristics. Surfaces may be viewed either directly or with magnification. They may be measured by devices such as profilometers which give a quantitative measurement of roughness. More recently, sophisticated techniques such as ellipsometry, low energy electron diffraction, Auger electron spectroscopy and scanning electron microscopy have been employed for characterizing surfaces. However, when used in an industrial environment all of these techniques have serious drawbacks. Most require the use of bulky, expensive instruments. Most of the advanced techniques require that the piece under study be placed in a high-vacuum chamber, thereby effectively limiting the size of the parts and the rate at which they may be examined.

Perhaps most critically, however, these techniques are not readily adapted to acceptance testing on an industrial scale by relatively unskilled personnel. For example, ellipsometry may be used to determine the thickness of an oxide coating formed on a surface by a particular heat treatment, but it is typically not practical to check by ellipsometry every piece subsequently given the same heat treatment. Instead, it must be assumed that uncontrolled variables do not enter the process and that each heat treatment is successful in producing the desired surface. In some industrial operations such as coating a surface with adhesives, there simply is no way to predict when problems such as isolated patches of grease on a previously cleaned surface may arise. There is no readily available means to discriminate between such patches of grease that will not interfere with painting of the surface, and those which might prevent application of an acceptable coating.

Additionally, when utilizing many highly advanced surface characterization techniques it is difficult to know whether the characteristic measured is really important and determinative of acceptability of the surface. That is, measurements may be made of surface characteristics, but one is then faced with the problem of deciding whether that measurement is at all relevant to the planned usage of the material and, if so, what the limits of acceptable variation of the measured characteristic might be in order to ensure success of the subsequent processing.

There has therefore existed a continuing need for a surface monitoring apparatus and associated monitoring technique which is sensitive to microscopic surface charateristics, is measurable by relatively inexpensive and compact apparatus, does not require that the surface to be studied be placed in a vacuum chamber, and, most importantly, allows the development of acceptability and quality control tests which may be utilized by relatively unskilled personnel for testing large surfaces of numbers of parts. The present invention fulfills this need, and further provides related advantages.

SUMMARY OF THE INVENTION

The present invention provides an apparatus and technique for characterizing surfaces by optically stimulated electron emission, and making acceptability and quality control determinations of such surfaces in an industrial environment. The instrument is compact, may be utilized in air, and is readily adapted to different surface areas, configurations and characteristics to be measured. With this invention, the quality assurance and quality control of surface dependent industrial operations is greatly facilitated.

In accorance with the invention, an instrument for measuring optically stimulated electron emission includes an ultraviolet light source, an electrical biasing means for creating an electrical potential between the instrument and the surface being studied to cause photoemitted electrons to flow from the surface to the instrument, a charge collector, an amplifier or electrometer to produce a signal proportional to the current of photoemitted electrons, and electronic circuitry to store values of acceptability limits on the current of photoemitted electrons, and to determine and signal the existence of photoelectron currents not within the acceptability limits. In one embodiment, multiple ultraviolet light sources and collectors are utilized, and additional electronic circuitry multiplexes the several photoelectron currents to utilize some common electronic components for measuring all of the currents.

In the preferred embodiment, each ultraviolet light source, collector and amplifier, along with supporting circuitry, are packaged together in a sensing unit having a maximum diameter of about two inches and an overall length of about eight inches. The balance of the components may be remotely positioned and connected to the housing by cables, thereby making the instrument portable and easy to use.

In use as a quality assurance monitor, the instrument may first be used to measure photoelectron currents from a variety of surfaces. The surfaces are then characterized as either acceptable or unacceptable for particular applications. As an example, if a surface were to be painted and contaminants on the surface interfere with the painting process, a number of surfaces could be prepared with varying levels of contamination, measured to determine the photoelectron current, and then painted. Surfaces having little or no contamination would presumably result in acceptable final painted products, while increasing amounts of contamination would increasingly impair the paint quality. A judgment would be made as to a level of acceptable contamination, and the photoelectron current corresponding to that level entered into the detector circuitry. Unacceptably high levels of surface contamination could then be detected by inexperienced persons or automated quality control machinery by moving the instrument over the surface of production parts prior to painting until a warning signal was observed. The instrument may be utilized for a wide variety of surface monitoring applications, and this example is provided only for illustrative purposes and is not to be taken as limiting the scope of the invention and its utilization.

It will be appreciated from the foregoing that the present invention represents a significant advance in quality control procedures for evaluating surfaces of materials in industrial environments. The instrument is readily adaptable to a wide variety of industrial surface quality control procedures, allows the surface to be inspected in air, is compact, and is readily used in typical industrial environments. Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate embodiments of the invention. In such drawings:

FIG. 1 is a schematic drawing of an optical surface quality monitor made in accordance with the present invention;

FIG. 2 is an enlarged sectional elevational view of the sensor tube and amplifier head of the invention;

FIG. 3 is an enlarged fragmented sectional elevational view of a sensing unit adapted for inspecting surfaces near edges and corners.

FIG. 4 is a bottom plan view of the sensing unit of FIG. 3, taken generally along line 4—4;

FIG. 5 is an enlarged fragmented sectional elevational view of a sensing unit having a collector adapted for performing measurements of very small areas;

FIG. 6 is a bottom plan view of the sensing unit of FIG. 5, taken generally along line 6—6;

DETAILED DESCRIPTION OF THE PREFERRED EMBODIMENT

Figure 7:
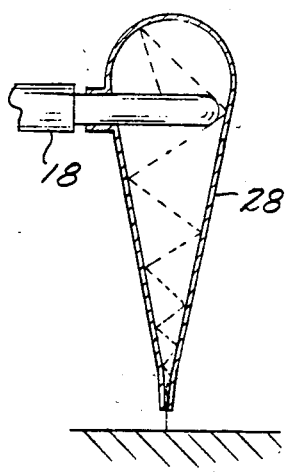
FIG. 7 is a sectional elevational view of a sensing tube configuration for concentrating the ultraviolet light beam to a fine point.

The present invention utilizes the principles of optically stimulated electron emission in air. Briefly, ultraviolet light directed against a surface largely passes through any surface films, contamination or other irregularity on the surface and strikes the underlying substrate. Photoelectrons are emitted from the surface, and some of the photoelectrons emitted from the surface diffuse through the air while others attach to oxygen atoms and diffuse as ions. The current of electrons and ions may be collected and measured. In many instances, the current is directly related to the physical properties found at the surface such as oxide thickness, contamination level, and mechanical condition of the surface. The collection of the low energy photoelectrons emitted from the surface does not require that the surface and measuring appartus be in a vacuum, as the electrons and ions readily diffuse through air. This technique is potentially applicable to characterization of photoemitting surfaces such as those of metals, semiconductors, many polymers and some ceramics.

In accordance with a preferred embodiment of the present invention and as schematically illustrated in FIG. 1, an optical surface quality monitor 10 includes a sensing unit 12 and a control unit 14, connected by a cable 16.

The sensing unit 12 includes an ultraviolet lamp 18 for directing a beam of ultraviolet light against a surface 20 whose properties are to be measured. A battery 22 positively biases a collector 24 located adjacent the surface 20 to attract photoelectrons emitted by the surface 20 when struck by the beam of ultraviolet light, as well as to attract negatively charged ions that may be formed by some of the photoelectrons emitted from the surface 20. The current of photoelectrons and negatively charge ions, together constituting a photoelectric current, received by the collector 24 is conducted to an amplifier 26 through a resistor 27 and the battery 22, wherein the photoelectron current level is amplified and converted to a voltage signal proportional to the photoelectron current, for transmission on the cable 16. Inasmuch as the sensing unit 12 may be located remotely from the control unit 14, tnhis amplification of the photoelectric voltage in the sensing unit 12 is preferred, to reduce the relative interference of electronic noise in the cable 16.

The elements of the sensing unit 12 are included in a housing, or, more preferably, in two detachable housings, a sensor tube 28 and an amplifier head 30. The sensor tube 28 contains the ultraviolet lamp 18 and the collector 24, while the resistor 27, battery 22, and amplifier 26 are located in the amplifier head 30. In normal operation, the two housings are attached as a single unit, but the sensor tube 28 may be detached from the amplifier head 30 for special applications requiring its more compact size. It is preferable that the two housings remain attached with the amplifier 26 in proximity to the collector 24 to minimize the introduction of extraneous electronic noise as the photoelectric current is conducted from the collector 24 to the amplifier 26.

The control unit 14 processes the amplified signal from the sensing unit 12 for display and for generating a warning signal to the operator in the event that the photoelectric signal varies from a preselected range of values. The amplified signal first passes through a low pass filter 32 to filter the high frequency component of the signal, which typically is electronic noise. The filtered photoelectric signal is provided to a display 34 for displaying the value of the voltage, and also to a threshold detector 36 for detecting any variation of the photoelectric signal from a preselected range.

The threshold detector 36 includes a low level limit detector 38 for determining whether the amplified photoelectric signal is less than a value set by adjusting a low-level variable resistor 40. In a similar fashion, a high-level detector 42 determines whether the amplified photoelectric current exceeds a value set by adjusting a high-level variable resistor 44. The range between the low and high limits defines an acceptance window or range for use in quality assurance or quality control testing, as will be more fully discussed below.

The outputs of the limit detectors 38 and 42 are OR-ed together, so that a limit signal is generated if the filtered photoelectric signal is not within the range between the selected low-level and high-level values. The limit signal is provided to an alarm-and-latch circuit 46 which provides an audio, visual, or other semipermanent indication to the operator of variation from the preselected limits, the signal continuing until a reset switch 48 is operated.

As illustrated in greater detail in FIG. 2, the sensing unit 12 includes two disconnectable housings, the amplifier head 30 and the sensor tube 28. The ultraviolet lamp 18 is mounted within the sensor tube 28, as by a pair of nonconducting spacers 50 such as teflon washers. The lower end of the sensor tube 28 is open, so that a beam of ultraviolet light is directed from the ultraviolet lamp 18 against the surface 20 being measured. The collector 24 for receiving the photoelectric current emitted from the surface 20 is mounted in a collector adaptor 52 which in turn is detachably joined to the lower end of the sensor tube 28. The collector 24 is formed of a metal having a convenient configuration, such as a wire mesh screen allowing the passage of ultraviolet light out of the sensor tube 28 but collecting the emitted photoelectric current.

A lead 54 is attached to the collector 24 by a connector 56. The lead 54 passes upwardly along the length of the sensor tube 28, within a shield 58 to minimize the introduction of electronic noise into the small photoelectric current. The lead 54 terminates in a quick disconnect connector 60, which electrically connects the sensor tube 28 to the amplifier head 30.

Within the amplifier head 30, one of several alternative resistors 62 is placed in series with the collector 24 and the amplifier 26 by a switch 64, to change the sensor sensitivity to emission, thereby changing the amplification factor of the instrument. The photoelectric current then passes through the battery 22 and the amplifier 26, wherein the photoelectric current is amplified and converted to a voltage level proportional to the photoelectron current and sufficient to allow transmission to the remotely placed control unit 14 through the cable 16, without the introduction of excessive levels of electrical noise.

Figure 11:
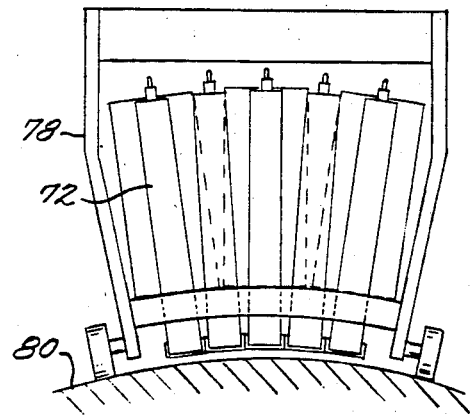
FIG. 11 is an elevational view of a plurality of sensing units mounted in a wheeled dolly.

In use, the sensing unit 12 is positioned adjacent the surface 20 being inspected, at a collector-to-surface distance mechanically fixed by a holder or other apparatus. For example, as shown in FIG. 11, the sensing unit 12 may be supported in a wheeled dolly that allows the sensing unit to be traversed over the surface while retaining the collector 24 at a fixed distance from the surface 20. While the absolute magnitude of the distance between the collector 24 and the surface 20 is not critical, the distance should remain substantially constant for any one series of measurements to avoid geometrically induced current variations.

The emitted photoelectric current is collected by the collector 24 and conducted to the amplifier 26 through one of the resistors 62 and the battery 22. The amplifier 26, resistor 62 and battery 22 together constitute an electrometer for producing a voltage signal proportional to the photoelectron current, and the voltage signal is then conducted through the cable 16 to the control unit 14 for subsequent analysis. The high frequency component of the amplified photoelectric current is filtered for display and for detection of any value which falls outside the acceptability window. If such a variance is detected, the limit signal activates the alarm-and-latch unit 46 to provide a positive signal of the variance to the operator. Alternatively, the filtered signal could be provided to a computer programmed to perform the quality assurance function.

In a preferred unit, the sensor tube 28 is a hollow nonconducting tube having dimensions of about 1 inch diameter and 6 inches long. The preferred dimensions of the collector adaptor 52 are 1 inch diameter by $\frac{1}{2}$ inch long. The preferred dimensions of the amplifier head 30 are 2 inches diameter by $4\frac{1}{2}$ inches long. The sensor tube 28 may be mechanically disconnected from the amplifier head 30 while maintaining electrical contact through a shielded cable and the quick connect disconnector 60, thereby leaving the sensing unit functional. However, any movement of the lead 54 may induce electronic noise, so that it is preferable that the sensor tube 28 and the amplifier head 30 remain mechanically connected.

The design and construction of the amplifier 26, low-pass filter 32, threshold detector 36, display 34, and alarm-and-latch unit 46 are conventional, and their separate constructions will be apparent to those skilled in the art. Preferably, the amplifier 26 has sufficient gain so that, in conjunction with selection of one of the resistors 62, the voltage signal transmitted on the cable 16 is in the range of several volts, such as 0–10 volts. The cable 16 is typically 6 feet long, but longer lengths may be used as needed, inasmuch as the amplified voltage signal is not greatly interfered with by ordinary electrical noise induced in the cable and most noise is filtered out by the low pass filter 32. The low-pass filter 32 preferably filters frequencies greater than about 10–20 Hertz. None of these specific values has been found to be critical to operation of the invention.

In one embodiment of the invention, a plurality, such as five, of independent sensing units are provided. Each sensing unit includes a dedicated amplifier, and the control unit includes a dedicated low pass filter and threshold detector for each sensing unit. The limit signals are OR-ed together to a single alarm-and-latch unit, inasmuch as variation of any one of the sensing units from its acceptability window signals an unacceptable surface condition. Dedicated displays need not be provided, since the operator typically can observe only a single display and because the display is ordinarily utilized only to evaluate signals falling outside the acceptance window. Accordingly, the filtered photoelectric current to be provided to the display may be multiplexed, with appropriate logic to select the sensing unit for display or to cycle the display serially through the multiple sensing unit signals. However, those skilled in the art will recognize that multiple sensing units may be electronically detected in a variety of ways, all consistent with the functioning of the optical surface quality monitor as disclosed herein.

In one mode of operation, the optical surface monitor may be utilized simply to measure the magnitude of photoelectric currents emitted from a surface. More commonly, the optical surface quality monitor is used to perform quality assurance and quality control functions in an industrial environment. In this latter usage, the instrument must first be calibrated to determine the voltage range of the acceptance window.

To calibrate the optical surface quality monitor, a series of samples are controllably prepared using as a variable one or more aspects of the surface preparation expected to vary during normal production operations. Controllably variable features may include, for example, coating thickness, type of contamination, degree of contamination, or surface roughness. The samples are evaluated for photoelectric currents using the optical surface quality monitor with the sensing unit held at a fixed distance above each surface, and the values recorded. The individual samples are then processed through the subsequent intended procedure, such as, for example, painting, bonding, microelectronic processing, or functioning as a bearing. The performance of the surfaces is evaluated in their intended roles or uses, and those surfaces judged to give acceptable performance separately classified as to their previously measured photoelectron emission levels, from those judged to give unacceptable performance. An acceptance range or window of photoelectric current is thereby defined, and the upper and lower limits of the acceptable window provided to the variable resistors 40 and 44, respectively.

With this calibration complete, unknown surfaces may be quality checked by relatively unskilled personnel, by traversing the sensing unit 12 over the unknown surface at the same fixed distance used for the calibration samples. Any occurrences of unacceptable surface conditions are detected by activation of the alarm-and-latch unit 46, and the operator may then correct the defect, such as by further cleaning of the surface 20, or may discard the piece if the defect is not readily corrected. In the preferred embodiment described herein, it has been found that the sensing unit 12 may be traversed over a surface at rates up to about one foot per second. Additionally, the evaluation of large surface areas is accelerated by the use of multiple sensing units as described previously herein.

The design of the sensing unit 12 allows substantial variation to facilitate specialized surface inspections. For example, FIGS. 3 and 4 illustrate a sensing unit specially adapted for inspecting surfaces near edges or corners. The collector 24 is made as a square array of collector wires 66, and a mask 68 is provides to screen a portion of the surface 20 from the beam of ultraviolet light. Using this configuration, the beam of ultraviolet light may be selectively directed against a specific area near an edge or corner of the surface, avoiding the introduction of spurious signals from walls or other undesired areas.

Figure 9:
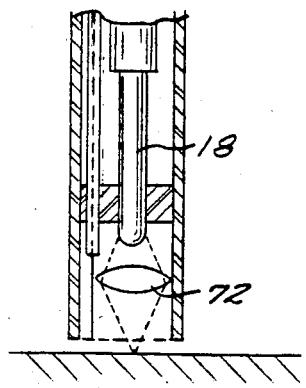
FIG. 9 is a fragmented sectional elevational view of a sensing unit for concentrating the ultraviolet light beam to a fine point.

The beam of ultraviolet light may also be directed against very small areas, allowing inspection of such small areas and also allowing the use of the sensing unit as a microscope for viewing very small areas. FIGS. 5 and 6 illustrate one approach, wherein the collector 24 is configured as a disk having an aperture 70 therethrough. The aperture allows only a fine beam of ultraviolet light to be directed against the surface, so that photoemitted electrons are produced only by the very small area illuminated. FIGS. 7 and 9 illustrate alternative approaches for directing an intensified beam of ultraviolet light against a surface 20. In the apparatus of FIG. 7, the inside of the sensor tube 28 is mirrored, and the sensor tube 28 is configured to focus a large portion of the ultraviolet light emitted from the lamp 18 against a single small area on the surface. FIG. 9 illustrates a sensing unit wherein a lens 72 directs a portion of the ultraviolet light against a small area on the surface. The forms of sensing unit illustrated in FIGS. 7 and 9 allow the beam of ultraviolet light to be directed against a smaller surface area than that of the apparatus of FIG. 5, and in addition allows a greater proportion of the total light emitted by the ultraviolet lamp 18 to be directed against the surface. In some applications, it is necessary that the beam of ultraviolet light directed against a small area have such a greater intensity as permitted by the apparatus of FIGS. 7 and 9, because the current of photoemitted electrons increases with increasing intensity of the incident ultraviolet light. As the area of emission is reduced, it is necessary that the intensity of the ultraviolet light be increased so as to produce a photoelectric emission current of sufficient magnitude to be detected and amplified properly in the presence of ordinary noise levels.

Figure 8:
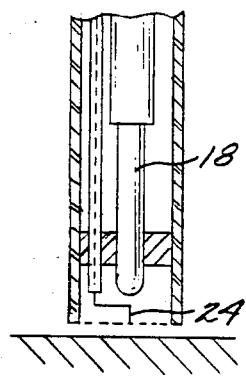
FIG. 8 is a fragmented sectional elevational view of a sensing unit having a fine wire collector.

In yet another approach for detecting the photoemission current from a small area, FIG. 8 illustrates an apparatus using a fine wire collector 24, wherein the beam of ultraviolet light is directed against a large surface, but use of the fine wire collector results in detection from a relatively limited portion of that surface.

Figure 10:
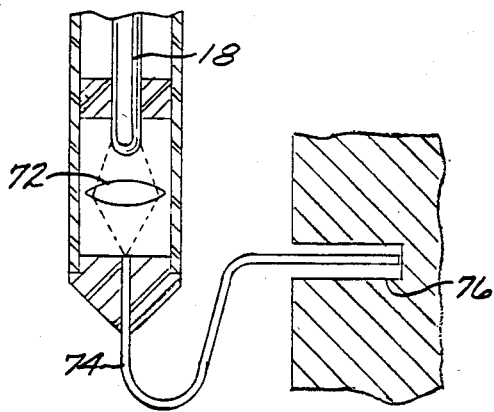
FIG. 10 is a fragmented sectional elevational view of apparatus for monitoring electron emission in holes or bores.

The apparatus of the present invention is also adaptable for inspecting areas which are normally inaccessable, or which have unusual configurations. FIG. 10 illustrates apparatus for inspecting the interiors of holes or bores. Ultraviolet light emitted by the lamp 18 is concentrated by a lens 72 to a relatively small area at the end of a light pipe 72. The light pipe 74 directs the beam of ultraviolet light against the surface of the interior of a hole 76, resulting in the production of photoelectrons. A photoelectric current is collected by a conducting silvered exterior coating on the light pipe 74 and thence conducted back to the sensing unit 12. Alternatively, a separate collector may be inserted into the hole 76 to collect the photoelectrons. In another approach for inspecting unusually configured surfaces, a plurality of sensing units 12 may be mounted in a carrier such as a wheeled dolly 78 for traversing across the surface. FIG. 11 illustrates an arrangement wherein five sensing units 12 are mounted in a wheeled dolly 78 which holds the sensing units 12 in a configuration so as to monitor a curved surface 80. By multiplexing the signals from the five sensing units 12, the surface condition of a large portion of the curved surface 80 may be evaluated in a single traverse of the dolly 78.

Figure 12:
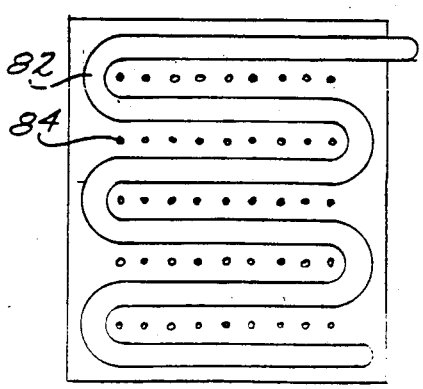
FIG. 12 is a bottom plan view of a sensing unit showing an ultraviolet lamp and sensor array arrangement.
Figure 13:
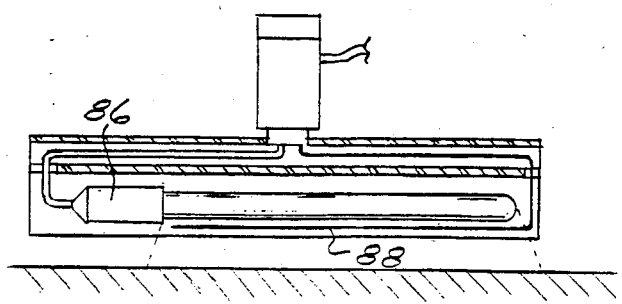
FIG. 13 is an enlarged fragmented sectional elevational view of a sensing unit for measuring large areas.

FIGS. 12 and 13 illustrate other approaches for monitoring relatively large surface areas utilizing the basic approach of the present invention. In FIG. 12, a single ultraviolet lamp 82 is configured to cover a large surface area, and the collector function is performed by an array of sensors 84. Again, the electronics multiplexes the signals from the sensors 84 to detect the photoemitted electrons from the relatively large area, thereby mapping the condition of the large area without moving the sensor array. In yet another approach, a large detection area is provided by configuring an ultraviolet lamp 86 to cover a large surface area, and providing a collector 88 which similarly covers a large surface area. In the approach illustrated in FIG. 13, the detection area is relatively wide, and long strips may be examined by translating the entire sensing unit. Other combinations of the components directly adapted to specialized inspection requirements will be readily apparent to those skilled in the art.

The apparatus of the invention may be used to monitor a variety of types of surfaces. Surfaces to be monitored should be electrically conducting or treatable to have sufficient electrical conductivity to allow production of a current of photoelectrons. For example, the surfaces of metals, semiconductors, many polymers and some ceramics may be readily evaluated without any treatment of the surface. A nonconducting material could be monitored for certain surface characteristics such as roughness by coating the surface with a very thin conducting layer. However, such pretreatments of nonconducting surfaces may alter some surface characteristics so that the applicability of the technique is limited.

For some materials, the photoemitting character of the surface 20 may change with time after first exposure to the ultraviolet light. It may therefore be desirable to provide circuitry so that the signal displayed on the display 34 is provided from a sampling taken at some point in time after first exposure, thereby minimizing the influence of the change in surface characteristics on the measurements. In one embodiment, illustrated in FIG. 1, an operator-activated switch 90 on the sensing unit 12 triggers a time-delay circuit 92, which has an operator adjustment 94 for setting the length of the delay. Thus, a period of time after the switch 90 is activated, the time delay circuit 92 sends a signal to a sample and hold circuit 96, which in turn samples the filtered signal from the low-pass filter 32. The sampled signal is then provided to the display 34. Alternatively, additional circuitry (not shown) may be provided to activate the time delay circuit 29 when the filtered signal from the low-pass filter 32 reaches a predetermined value. Such an alternative approach allows automatic triggering when the sensing unit 12 is brought near the surface 20, since only then does the filtered signal increase to a threshold level which can be determined during calibration.

It will now be appreciated that, through the use of this invention, the characteristics of surfaces may be evaluated by measurement of optically stimulated electron emission. An acceptance window for quality assurance and quality control purposes may be determined for various surface conditions, and then surfaces may be rapidly evaluated by relatively unskilled personnel or automated equipment in an industrial process environment. The equipment is compact, relatively inexpensive, readily adaptable to solving a wide variety of surface quality assurance problems, may be operated in air without the need for placing the surface in a vacuum, and need not contact the surface being measured.

Although a particular embodiment of the invention is described in detail for purposes of illustration, various embodiments may be made without departing from the spirit and scope of the invention. Accordingly, the invention is not to be limited except as by the appended claims.

What is claimed is:

1. An apparatus for performing quality assurance inspections of a surface comprising:

an ultraviolet light source disposed to direct ultraviolet light against the surface;
means for collecting photoelectrons emitted from the surface under the action of the ultraviolet light, said collection means including a collector to collect the current of emitted photoelectrons and biasing means to positively bias said collector with respect to the surface;
amplifier means for producing an amplified voltage signal proportional to the current of emitted photoelectrons, said ultraviolet light source, collection means and amplifier means together acting as a sensing unit to produce said amplified voltage signal;
a low-pass filter to filter out the high-frequency component of the amplified voltage signal, to produce a filtered voltage signal;
detector means for detecting when the filtered voltage signal falls outside preselected limits; and
means for signalling a variation of the filtered voltage signal outside the preselected limits, whereby an unacceptable surface is indicated.

2. The apparatus of claim 1, wherein said collector is circular with a diameter of about one inch.

3. The apparatus of claim 1, wherein said collector is rectangular and a portion of said collector is masked to allow inspection of corners and edges.

4. The apparatus of claim 1, further including means to limit the size of the area exposed to the ultraviolet light.

5. The apparatus of claim 1, further including means for focussing the ultraviolet light beam to a small area.

6. The apparatus of claim 1, wherein said collector is shaped as a fine wire.

7. The apparatus of claim 1, wherein said collector further comprises a plurality of independently measurable sensors.

8. The apparatus of claim 1, further comprising means for directing the ultraviolet light into a hole and the collector is sized for insertion into the hole.

9. The apparatus of claim 1, further comprising at least one additional sensing unit, each of said additional sensing units comprising as components thereof an ultraviolet light source, collection means and amplifier means, whereby each sensing unit produces a distinct amplified voltage signal for further processing.

10. Apparatus for measuring optically stimulated electron emission from a surface, comprising:

an ultraviolet light source;
means for collecting a photoelectric current emitted from the surface under the action of said light source;
electronic means for processing the collected photoelectric current signal and for determining whether the processed signal lies within preselected limits.

11. A process for performing quality assurance inspections to determine whether the surfaces of parts meet acceptance criteria releated to their ultimate use, comprising the steps of:

providing an apparatus for performing the inspection, said apparatus including an ultraviolet lamp for directing ultraviolet light against a surface, a collector for collecting the current of photoelectrons and negatively charged ions produced under the action of the ultraviolet light on the surface, an amplifier for producing an amplified signal proportional to the current of photoelectrons and ions, and threshold detector means for determining whether the amplified signal lies between selected values;

calibrating the apparatus to determine the range of values of surface characteristics producing acceptable performance in the ultimate use of the part, as measured by the current of photoelectrons and negatively charged ions from parts having acceptable performance in their ultimate use;

introducing the range of acceptable values into the threshold detector means; and measuring the surfaces of production parts using the apparatus, whereby unacceptable surface characteristics of the parts are indicated by variance of the current of photoelectrons and negatively charged ions from the previously introduced range of acceptable values.

12. The process of claim 11, wherein said apparatus further includes a low-pass filter for filtering the amplified signal prior to introduction into the threshold detector and indicating a variance of the current of photoelectrons and negatively charged ions from the range of acceptable values.

13. The process of claim 11, wherein said step of calibrating comprises:

preparing a series of sample parts having a range of surface characteristics expected to be encountered in production;

measuring the current of photoelectrons and negatively charged ions from each of the sample parts;

testing the sample parts for suitability in their ultimate intended use; and correlating the suitability in intended use with measured photoelectric current to develop an acceptability criterion as to acceptable photoelectric current.

* * * * *